US008442281B2

(12) United States Patent
Jung et al.

(10) Patent No.: US 8,442,281 B2
(45) Date of Patent: May 14, 2013

(54) ARTIFICIALLY DISPLAYING INFORMATION RELATIVE TO A BODY

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Clarence T. Tegreene, Bellevue, WA (US); Lowell L. Wood, Jr., Livermore, CA (US)

(73) Assignee: The Invention Science Fund I, LLC, Bellvue, WA (US)

( * ) Notice: Subject to any disclaimer, the term of this patent is extended or adjusted under 35 U.S.C. 154(b) by 1399 days.

(21) Appl. No.: 11/414,149

(22) Filed: Apr. 28, 2006

(65) Prior Publication Data
US 2007/0253614 A1 Nov. 1, 2007

(51) Int. Cl.
*G06K 9/00* (2006.01)

(52) U.S. Cl.
USPC .......................................................... 382/128

(58) Field of Classification Search ................. 382/103, 382/128, 131, 132; 283/85, 88, 89, 91, 92; 235/462.01–462.05, 462.08, 462.09, 462.1, 235/462.11; 347/110, 107; 353/28; 106/31.14, 106/31.15; 600/114, 117, 417; 606/130; 345/7, 8, 9; 715/863
See application file for complete search history.

(56) References Cited

U.S. PATENT DOCUMENTS

| 2,851,805 | A | * | 9/1958 | Allen ............................ 132/319 |
| 4,515,773 | A | * | 5/1985 | Herlihy ........................... 424/59 |
| 4,567,898 | A |   | 2/1986 | Plugge et al. |
| 4,594,276 | A | * | 6/1986 | Relyea ......................... 428/42.1 |
| 4,610,806 | A | * | 9/1986 | Rosen ...................... 252/301.16 |
| 4,614,366 | A | * | 9/1986 | North et al. ..................... 283/70 |
| 4,817,622 | A |   | 4/1989 | Pennypacker et al. |
| 4,887,605 | A |   | 12/1989 | Angelsen et al. |
| 4,947,867 | A | * | 8/1990 | Keeton .......................... 128/846 |
| 4,951,151 | A | * | 8/1990 | Sorenson et al. ............. 348/744 |
| 5,052,418 | A | * | 10/1991 | Miller ........................... 132/319 |
| D342,283 | S | * | 12/1993 | McGill .......................... D20/11 |
| 5,436,115 | A | * | 7/1995 | Mullis ........................... 430/338 |
| 5,526,812 | A | * | 6/1996 | Dumoulin et al. ........... 600/407 |
| 5,715,836 | A | * | 2/1998 | Kliegis et al. ................ 600/425 |
| 5,769,078 | A | * | 6/1998 | Kliegis .......................... 600/407 |
| 5,772,593 | A | * | 6/1998 | Hakamata .................... 600/407 |
| 5,792,147 | A | * | 8/1998 | Evans et al. ................... 606/130 |
| 5,810,757 | A |   | 9/1998 | Sweezer, Jr. et al. |
| 5,837,042 | A | * | 11/1998 | Lent et al. .................. 106/31.14 |
| 5,837,645 | A | * | 11/1998 | Fuerst et al. .................. 503/201 |
| 5,958,560 | A | * | 9/1999 | Ewan ......................... 428/32.24 |
| 5,978,696 | A | * | 11/1999 | VomLehn et al. ............ 600/411 |
| 6,026,814 | A |   | 2/2000 | LaFontaine et al. |
| 6,286,682 | B1 | * | 9/2001 | d'Arbelles ..................... 206/570 |
| 6,306,409 | B1 | * | 10/2001 | Ogawa et al. ................. 424/401 |

(Continued)

OTHER PUBLICATIONS

PCT International Search Report; International Application No. PCT/US 07/10310; pp. 1-2; dated Mar. 5, 2008.

(Continued)

*Primary Examiner* — Vikkram Bali

(57) ABSTRACT

A method and system are described for generating a pattern indicating at least medical information related to an individual's body; and invoking circuitry for displaying at least the generated pattern on one or more surfaces on the individual's body.

31 Claims, 10 Drawing Sheets

U.S. PATENT DOCUMENTS

| | | | |
|---|---|---|---|
| 6,312,124 B1* | 11/2001 | Desormeaux | 347/109 |
| 6,314,311 B1* | 11/2001 | Williams et al. | 600/425 |
| 6,317,616 B1* | 11/2001 | Glossop | 600/407 |
| 6,418,339 B1* | 7/2002 | Essenpreis et al. | 600/476 |
| 6,470,891 B2* | 10/2002 | Carroll | 128/897 |
| 6,503,195 B1* | 1/2003 | Keller et al. | 600/160 |
| 6,531,118 B1* | 3/2003 | Gonzalez et al. | 424/59 |
| 6,543,893 B2* | 4/2003 | Desormeaux | 347/109 |
| 6,599,247 B1* | 7/2003 | Stetten | 600/443 |
| 6,608,884 B1* | 8/2003 | Mazess et al. | 378/98 |
| 6,622,733 B2* | 9/2003 | Saksa | 132/200 |
| 6,690,964 B2* | 2/2004 | Bieger et al. | 600/424 |
| 6,694,164 B2* | 2/2004 | Glossop | 600/407 |
| 6,814,760 B2* | 11/2004 | Anderson et al. | 8/404 |
| 6,889,075 B2* | 5/2005 | Marchitto et al. | 600/473 |
| 6,961,608 B2* | 11/2005 | Hoshino et al. | 600/423 |
| 7,016,522 B2 | 3/2006 | Bani-Hashemi | |
| 7,050,845 B2* | 5/2006 | Vilsmeier | 600/427 |
| 7,104,996 B2* | 9/2006 | Bonutti | 606/86 R |
| 7,131,446 B2* | 11/2006 | Tang et al. | 128/898 |
| 7,136,518 B2* | 11/2006 | Griffin et al. | 382/133 |
| 7,212,109 B2* | 5/2007 | Morita et al. | 340/539.12 |
| 7,317,955 B2* | 1/2008 | McGreevy | 700/83 |
| 7,389,928 B2* | 6/2008 | Lubow | 235/462.01 |
| 7,567,833 B2* | 7/2009 | Moctezuma De La Barrera et al. | 600/424 |
| 7,648,364 B2* | 1/2010 | Dauga et al. | 434/100 |
| 2001/0056358 A1* | 12/2001 | Dulong et al. | 705/2 |
| 2003/0184081 A1* | 10/2003 | Carlson, II | 283/67 |
| 2004/0082850 A1 | 4/2004 | Bonner et al. | |
| 2004/0122443 A1* | 6/2004 | Berryman et al. | 606/116 |
| 2004/0152975 A1* | 8/2004 | Blevis | 600/427 |
| 2004/0207652 A1* | 10/2004 | Ratti et al. | 345/697 |
| 2004/0236315 A1* | 11/2004 | Hered | 606/1 |
| 2005/0016448 A1* | 1/2005 | Dilou | 118/301 |
| 2005/0049624 A1 | 3/2005 | Francese et al. | |
| 2005/0085725 A1 | 4/2005 | Nagar et al. | |
| 2005/0159759 A1* | 7/2005 | Harbaugh et al. | 606/130 |
| 2005/0172852 A1* | 8/2005 | Anderson et al. | 106/31.03 |
| 2005/0182307 A1 | 8/2005 | Currie et al. | |
| 2005/0197574 A1 | 9/2005 | Eberle et al. | |
| 2005/0234322 A1* | 10/2005 | Lober | 600/407 |
| 2005/0251152 A1* | 11/2005 | Herweck et al. | 606/116 |
| 2005/0255299 A1* | 11/2005 | Yu | 428/195.1 |
| 2005/0279368 A1* | 12/2005 | McCombs | 128/897 |
| 2006/0067899 A1* | 3/2006 | Tanemo | 424/63 |
| 2006/0181482 A1* | 8/2006 | Iaquinto | 345/8 |
| 2006/0224151 A1* | 10/2006 | Waaler | 606/34 |
| 2006/0229551 A1* | 10/2006 | Martinez et al. | 604/67 |
| 2006/0235849 A1* | 10/2006 | Schmidt et al. | 707/7 |
| 2006/0236470 A1* | 10/2006 | Sabnis et al. | 8/405 |
| 2007/0032846 A1* | 2/2007 | Ferren et al. | 607/89 |
| 2007/0048340 A1* | 3/2007 | Ferren et al. | 424/401 |
| 2007/0148111 A1* | 6/2007 | Simpson | 424/63 |
| 2007/0225550 A1* | 9/2007 | Gattani et al. | 600/101 |
| 2010/0074488 A1* | 3/2010 | Ishikawa et al. | 382/128 |

OTHER PUBLICATIONS

Ericson, Gwen; "Smart wristband designed to prevent wrong-site surgery"; Washington University in St. Louis; bearing a date of Aug. 9, 2005; pp. 1-2; located at: http://mednews.wustl.edu/news/page/print/5547.html.

* cited by examiner

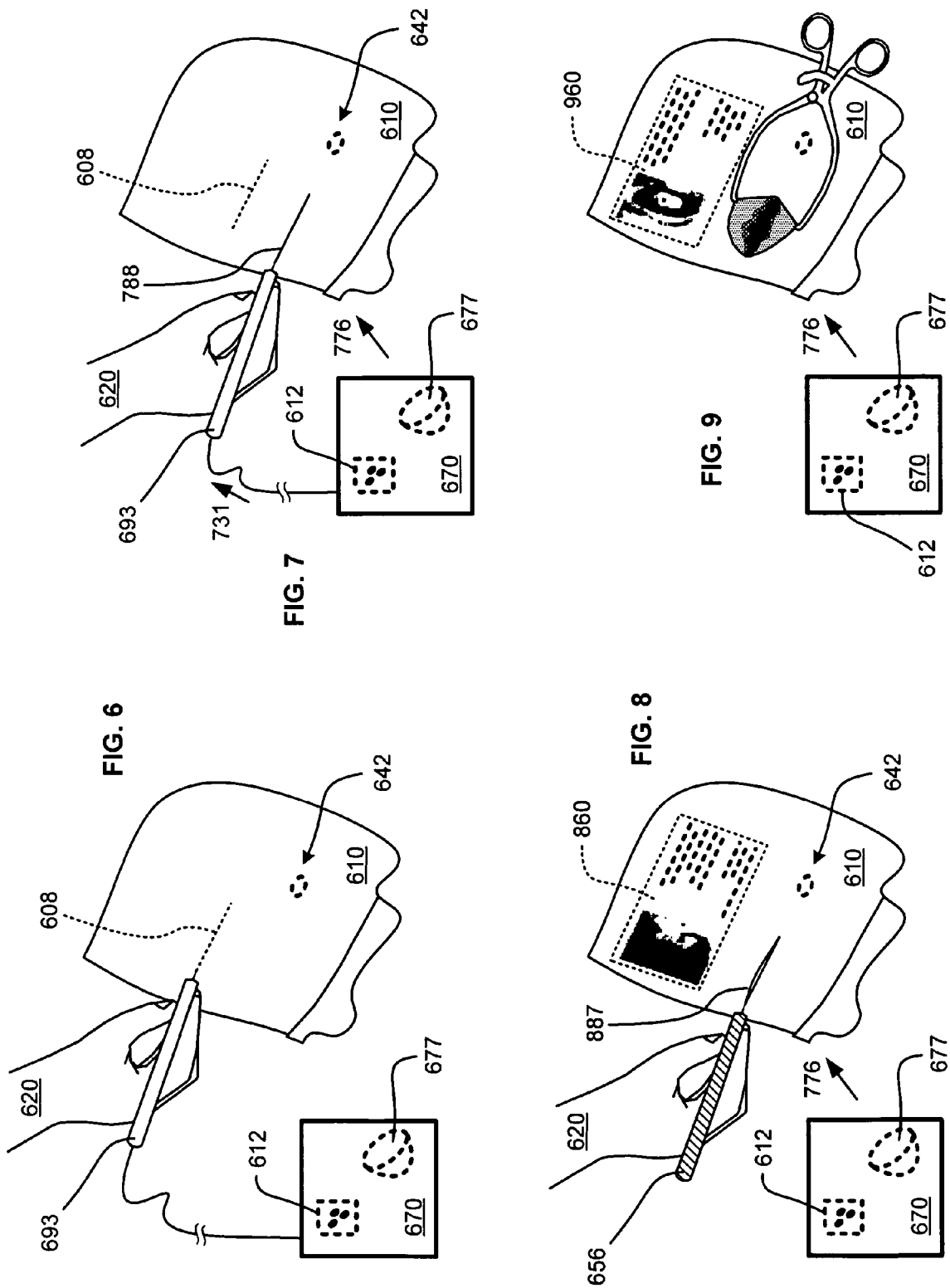

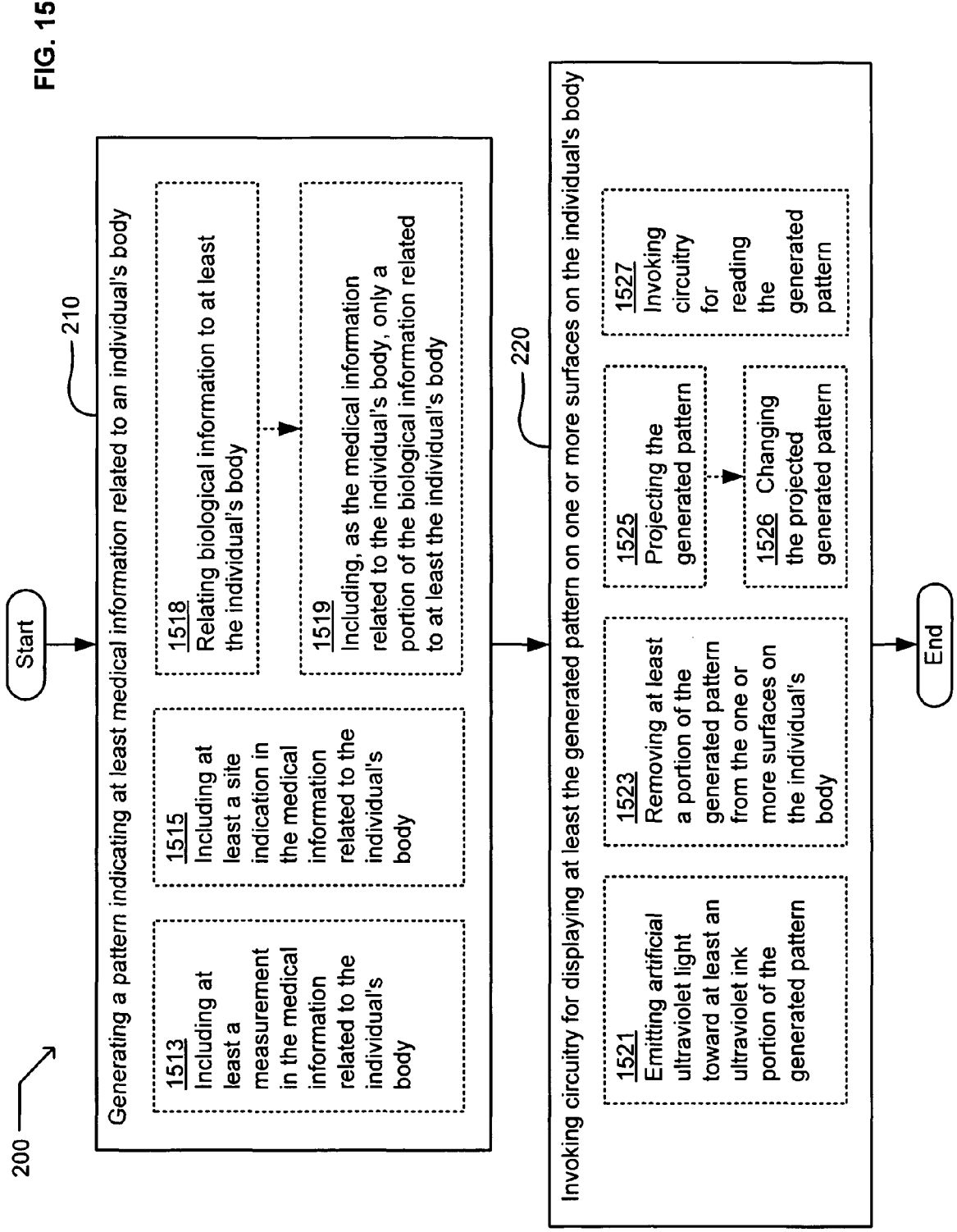

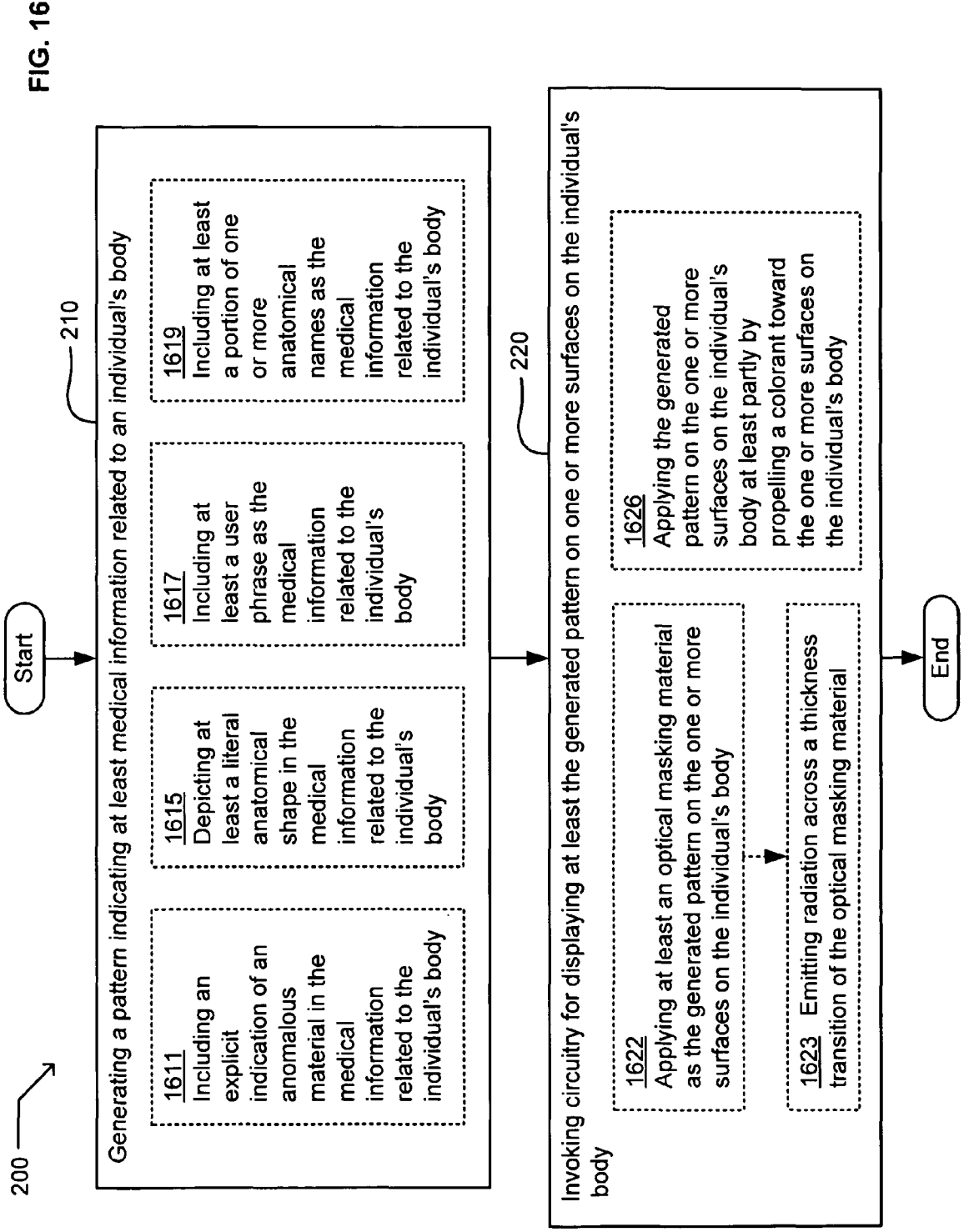

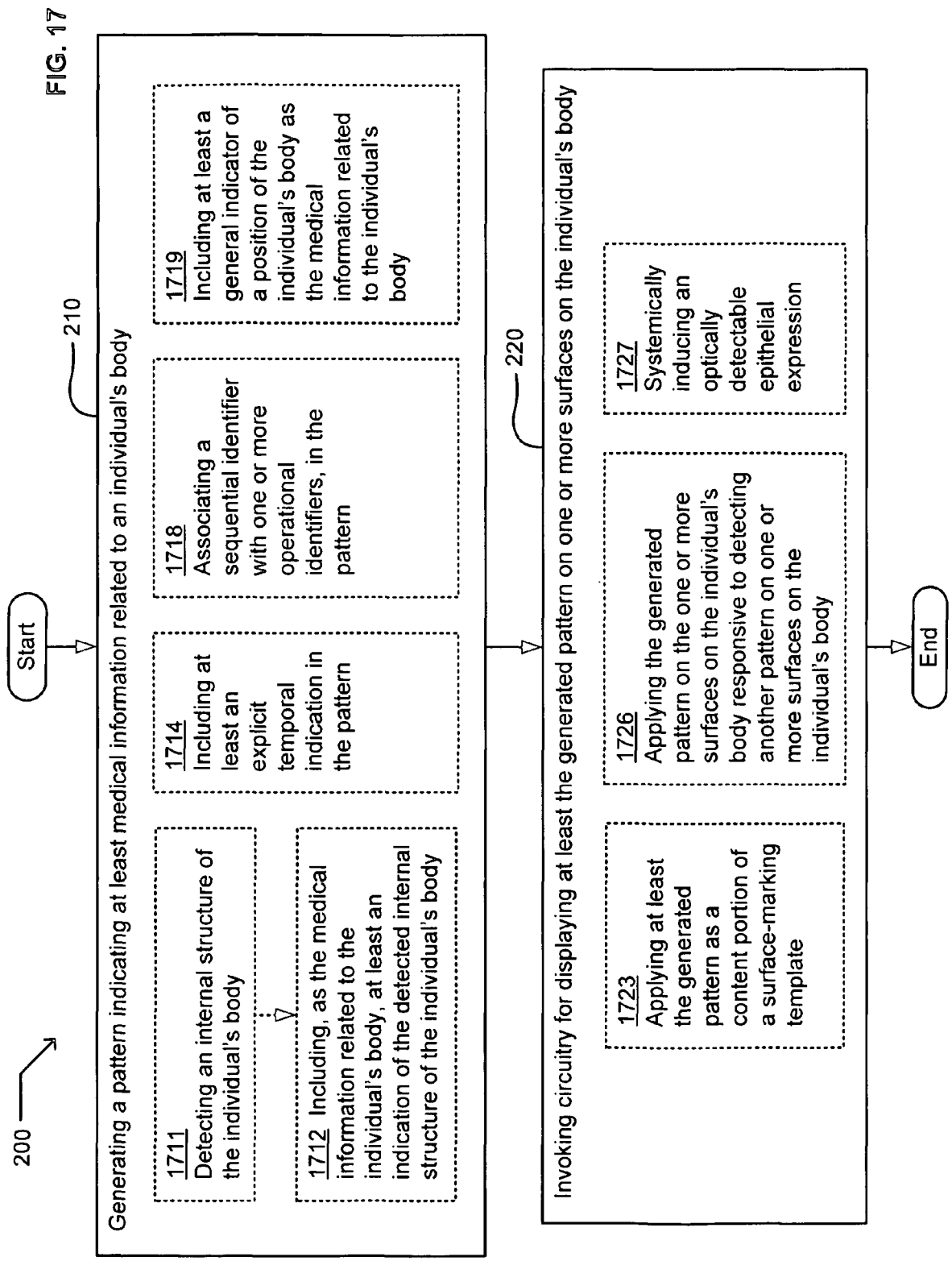

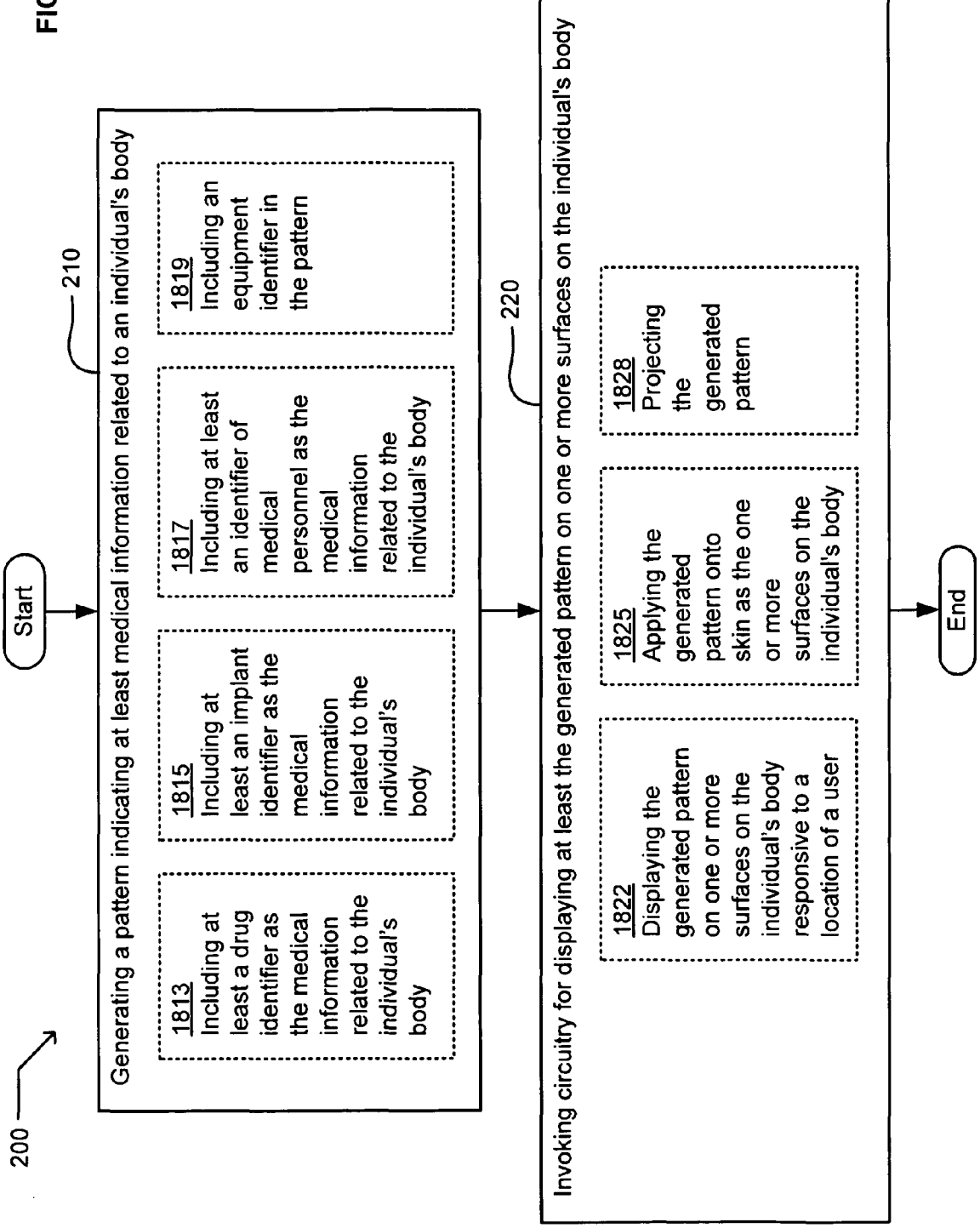

ARTIFICIALLY DISPLAYING INFORMATION RELATIVE TO A BODY

CROSS-REFERENCE TO RELATED APPLICATIONS

The present application is related to the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

1. For purposes of the USPTO extra-statutory requirements, the present application relates to U.S. patent application Ser. No. 11/414,164, entitled IMAGING VIA BLOOD VESSELS, naming Edward K. Y. Jung, Eric C. Leuthardt, Royce A. Levien, Robert W. Lord, Mark A. Malamud, John D. Rinaldo, Jr., Clarence T. Tegreene and Lowell L. Wood, Jr. as inventors, filed 28, Apr. 2006.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

An embodiment provides a method. In one implementation, the method includes but is not limited to generating a pattern indicating at least medical information related to an individual's body and invoking circuitry for displaying at least the generated pattern on one or more surfaces on the individual's body. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for generating a pattern indicating at least medical information related to an individual's body and invoking circuitry for displaying at least the generated pattern on one or more surfaces on the individual's body. In addition to the foregoing, other system aspects are described in the claims, drawings, and text forming a part of the present disclosure.

In addition to the foregoing, various other embodiments are set forth and described in the text (e.g., claims and/or detailed description) and/or drawings of the present description.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 5-9 each depicts another exemplary environment in which one or more technologies may be implemented.

FIGS. 14-18 each depict several variants of the flow of FIG. 2.

DETAILED DESCRIPTION

Figure 2:
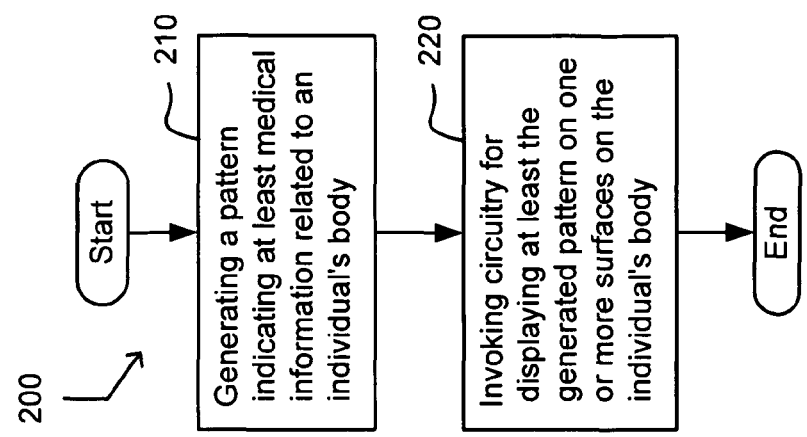
FIG. 2 depicts a high-level logic flow of an operational process.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
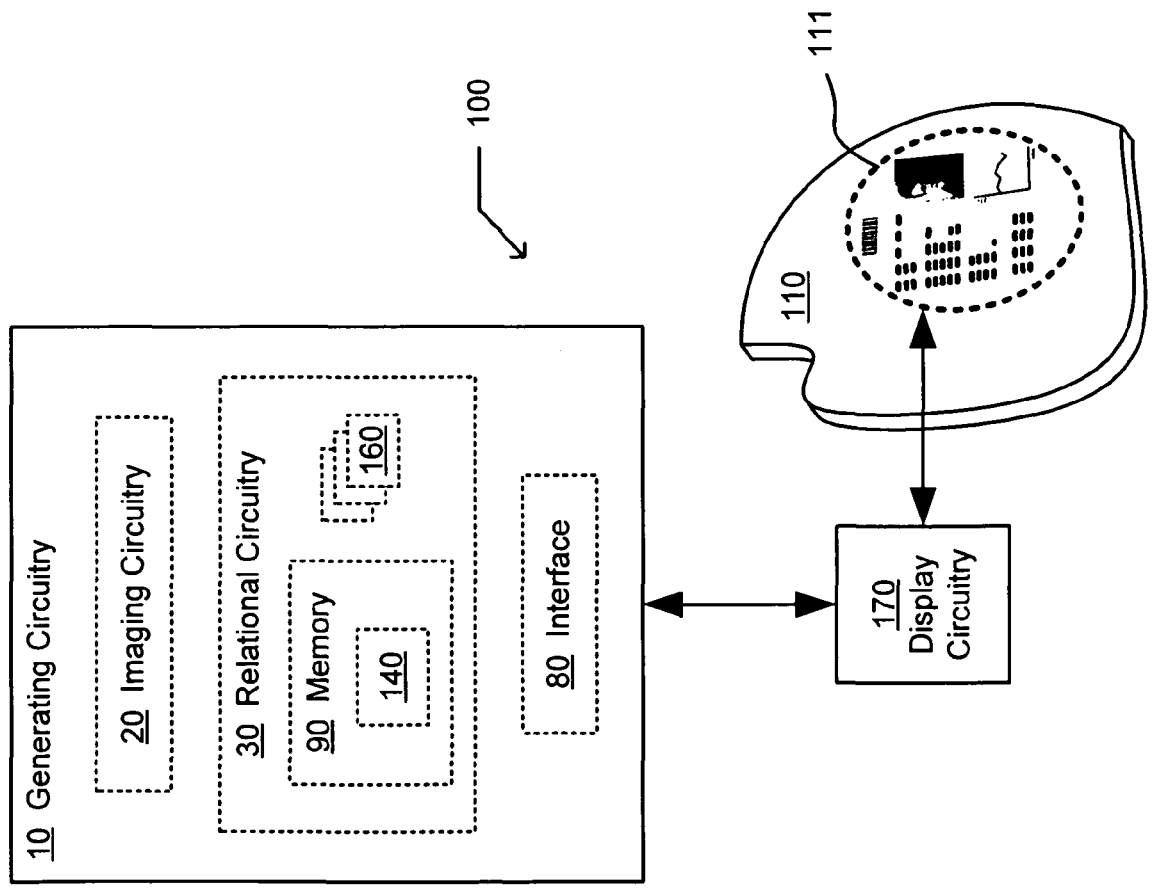
FIG. 1 depicts an exemplary environment in which one or more technologies may be implemented.

Referring now to FIG. 1, there is shown an exemplary environment in which one or more technologies may be implemented. As shown system 100 comprises generating circuitry 10 and display circuitry 170 configured for displaying one or more patterns at one or more treatment, testing, or other sites (as image 111 on a head, appendage, or other portion of an individual's body 110). In some embodiments, as exemplified below, "individual" refers to a human individual, living or otherwise, or a single mammal or other animal in a population. Also in some embodiments, "circuitry" comprises amplifiers, logic, or other active elements coupled by conduits.

Generating circuitry 10 can include one or more of imaging circuitry 20, relational circuitry 30, or interface 80. (In some variants, generating circuitry 10 contains display circuitry 170 operatively coupled to a power supply, not shown.) Relational circuitry 30 can include one or more images 160 and a data handling mechanism (memory 90, e.g.) containing one or more databases 140.

Those skilled in the art will appreciate that image 111 adequately shows an inclusion of text (on the left, as shown), a face or other recognizable portion of the individual's body (in the upper right), a barcode (at the top), and a data plot (in the lower right). Other aspects of the content of image 111 are incidental and not significant except as described below.

Referring now to FIG. 2, there is shown a high-level logic flow 200 of an operational process. Operation 210 describes generating a pattern indicating at least medical information related to an individual's body (e.g. imaging circuitry and/or relational circuitry 30 electronically generating a template or other pathology-indicative language or shape for application to a patient's skin). In some embodiments, the image is generated to complement or supersede one or more other patterns.

Operation 220 describes invoking circuitry for displaying at least the generated pattern on one or more surfaces on the individual's body (e.g. interface 80 invoking display circuitry 170 to apply image 111 to an individual's body). In some embodiments, the generated pattern is first applied to a template or otherwise projected, for example, responsive to input from one or more users.

Figure 3:
FIG. 3 depicts display circuitry in which one or more technologies may be implemented.

Referring now to FIG. 3, there is shown display circuitry 370 that can implement display circuitry 170 of FIG. 1 in some embodiments, as described below. Display circuitry 370 can include one or more of interface 373, projection circuitry 374, propulsion circuitry 381, drip control 385, printer 386, processing circuitry 390, user interface 391, or sensor circuitry 396. Projection circuitry 374 can include one or more of laser 376, emitter, 377, or update circuitry 379. Propulsion circuitry 381 can comprise applicator 383. Printer 386 can comprise one or more of alignment component 388 or content component 389. User interface 391 can comprise one or more of input device 393, query circuitry 394, or screen 395. Sensor circuitry 396 can comprise one or more of image capture circuitry 397 or image processing circuitry 398.

Figure 4:
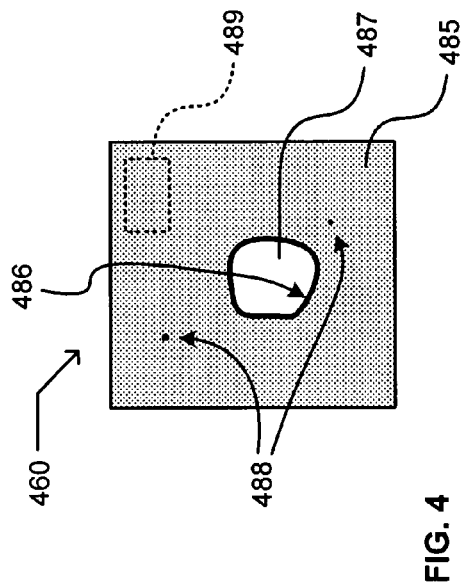
FIG. 4 depicts a template in which one or more technologies may be implemented.

Referring now to FIG. 4, there is shown an exemplary environment in which one or more technologies may be implemented. As shown template 460 comprises a generated pattern such as can be produced by printer 386. Alignment component 388 can, for example, comprise marks 488 that facilitate accurate placement of template 460 in the individual's body. Masking material 485 substantially covers template 460 except in one or more holes 487 each having a perimeter 486 at which the thickness of masking material 485 changes sharply. Template 460 may further include content component 489 containing, for example, logistical data or other medical data as described herein.

Figure 5:
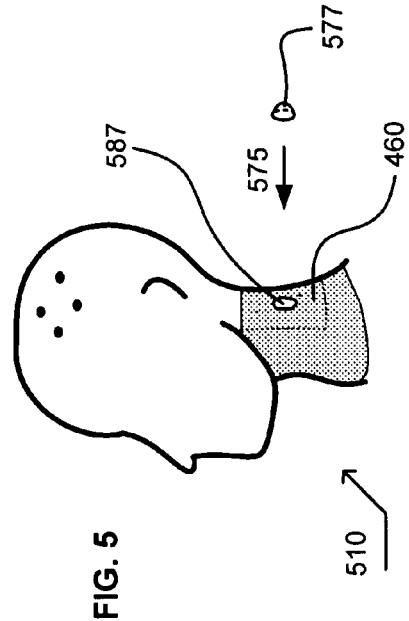

Referring now to FIG. 5, there is shown another exemplary environment in which one or more technologies may be implemented. Shown there is treatment area 587 an individual's body 510 to which template 460 has been applied, such as by an adhesive. For example, the masking material 485 may be or be coated with an adhesive applied by printer 386. In administering a treatment by operation 220, lamp 577 displays an electromagnetic or other treatment energy 575 that is at least partly shielded by masking material 485 (e.g. from a covered portion of the neck). In some embodiments, the generated pattern (information bearing non-uniformity, e.g.) recited in operation 220 is incidental to using the masking material for directing a more penetrating beam (infrared or lower frequency energy, X-ray energy, or the like, e.g.) to a treatment target inside the individual's body. In some embodiments, the treatment template itself contains a medication selectively applied substantially only to one or more target surfaces on the individual's body.

Referring now to FIG. 6, there is shown another exemplary environment in which flow 200 may be implemented. As shown display circuitry 670 can implement display circuitry 170 of FIG. 1 in some embodiments as described herein. Display circuitry 670 can include one or more of projector 677, sensors 612, and stylus 693. Before an operation in which surgeon 620 seeks to access internal anomaly 642 of patient 610, surgeon 620 can designate a potential incision site 608. Surgeon 620 can draw potential incision site 608, in some embodiments, in an ink readable by sensors 612. Alternatively or additionally, sensors 612 can record the motion of stylus 693 across the potential incision site 608. Surgeon 620 can make a dry run of a critical incision in a low pressure situation merely to practice, for example, or can in some circumstances consider a variety of potential incisions, for example from a different viewing angle or via a three dimensional modeling program (not shown).

Referring now to FIG. 7, there is shown a related environment in which one or more technologies may be implemented. As shown circuitry 670 can be used with stylus 693 in a different position than that of FIG. 6, which can be determined in a variety of ways. After determining that site 608 is unsatisfactory, in one scenario, surgeon 620 simply keeps tracing along other potential incision sites (not shown). Each site can supersede the previous one until an approval indication of pattern 788 is received (through a speech interface, e.g.).

In a second scenario, display circuitry 670 gives a warning, approval, or other feedback responsive to one or more potential incision sites the surgeon 620 proposes. For example, the feedback may come from an expert system helping the surgeon to perform an unfamiliar surgery, for example. Alternatively or additionally, display circuitry 670 give one or more consulting specialists a substantially live view or a specific indication of potential incision site 608 as a more specific basis upon which to provide feedback. Circuitry 670 can then relay feedback from the specialist(s) to surgeon 620, for example, by an auditory interface.

In a third scenario, display circuitry 670 acquires data representative of pattern 788, such as from an expert system or by one of the above-indicated scenarios. Display circuitry 670 can make pattern 788 visible to surgeon 620, for example, by using its knowledge of pattern 788 and of the individual's body location (obtained from sensor 612, e.g.) and invoking projector 677 to project energy 776 forming pattern 788.

In a fourth scenario, display circuitry 670 makes pattern 788 visible to surgeon 620 by projecting pigment-containing fluid 731 via stylus 693. Several variants of these scenarios are described below with reference to FIGS. 14-18.

Referring now to FIG. 8, there is shown display circuitry 670 with surgeon 620 having used scalpel 656 to form incision 887 along pattern 788. Those skilled in the art will appreciate that image 860 can optionally be provided on a surface of individual's body 610 near an intended incision site (pattern 788, e.g.) or otherwise oriented toward surgeon 620. As shown, image 860 adequately shows at least text (on the left of surgeon 620) and a face or other recognizable portion of the individual's body (on the surgeon's right). Other aspects of the content of image 860 as shown are incidental and not significant except as described below. In some embodiments, for example, image 860 can include notes from the remote specialist(s) from the above-described "second scenario."

Referring now to FIG. 9, there is shown an exemplary environment in which one or more technologies may be implemented for triggering a transition from the environment of FIG. 8. As shown FIG. 9 shows display circuitry 670 with surgeon 620 having opened incision 887 for accessing internal anomaly 642. Responsive to a user action (a nurse pressing a key or otherwise entering a command, e.g.), display circuitry 670 has caused projector 677 to remove image 860 and replace it with image 960. As shown, image 860 adequately shows replacement text (on the left of surgeon 620) and a sketch or other anatomical image (on the surgeon's right). Other aspects of the content of image 960 as shown are incidental and not significant except as described below.

Figure 10:
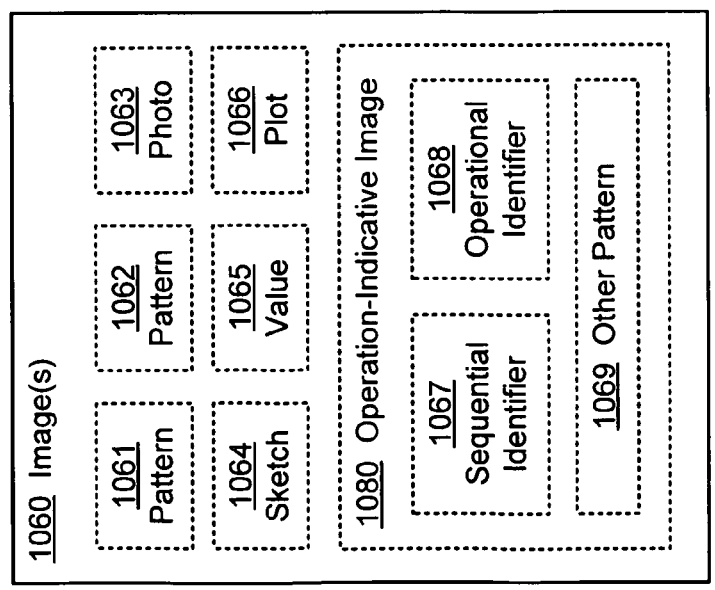
FIG. 10 depicts image(s) in which one or more technologies may be implemented.

Referring now to FIG. 10, there is shown a related environment in which one or more technologies may be implemented. As shown image(s) 1060 can be displayed within image 111 or image 860, handled as images 160 of FIG. 1, or otherwise described herein. Image(s) 1060 can include one or more of pattern 1061, pattern 1062, photo 1063, sketch 1064, value 1065, plot 1066, or operation-indicative image 1080. Operation-indicative image 1080 can include one or more of sequential identifier 1067, operational identifier 1068, or other pattern 1069.

Figure 11:
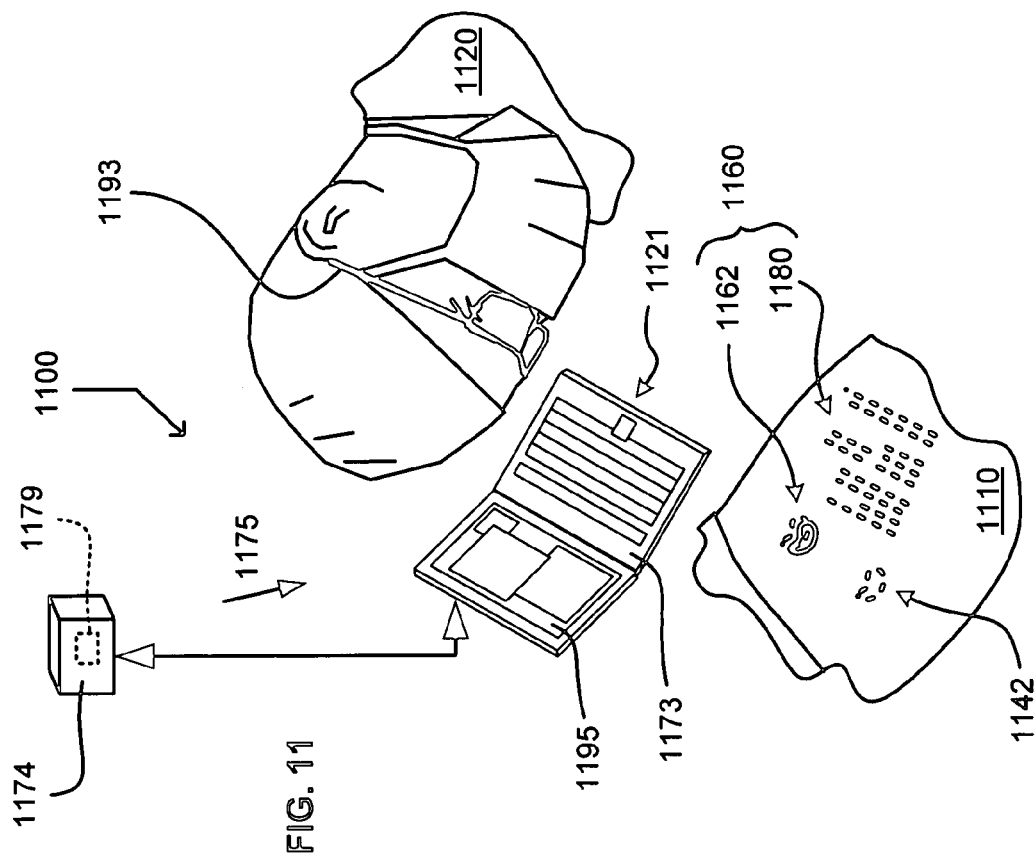
FIG. 11 depicts another exemplary environment in which one or more technologies may be implemented.

Referring now to FIG. 11, there is shown a related environment in which one or more technologies may be implemented. As shown system 1100 comprises hub 1173 operatively coupled to projector 1174. Projector 1174 can transmit projection 1175 onto one or more surfaces of individual's body 1110, optionally responsive to update circuitry 1179. Hub 1173 can respond to glasses 1193 and one or more other input device(s) 1121 to display information on screen 1195 or via projector 1174. Optionally screen 1195 complements image(s) 1160, which can include one or more of verbal image 1180 or pattern 1162. Pattern 1162 can indicate to user 1120 a location of target 1142. Those skilled in the art will appreciate that image 1180 can include text having a font size and orientation suitable for reading by user 1120. Other aspects of the content of image 1180 are incidental and not significant, except as described herein.

Figure 12:
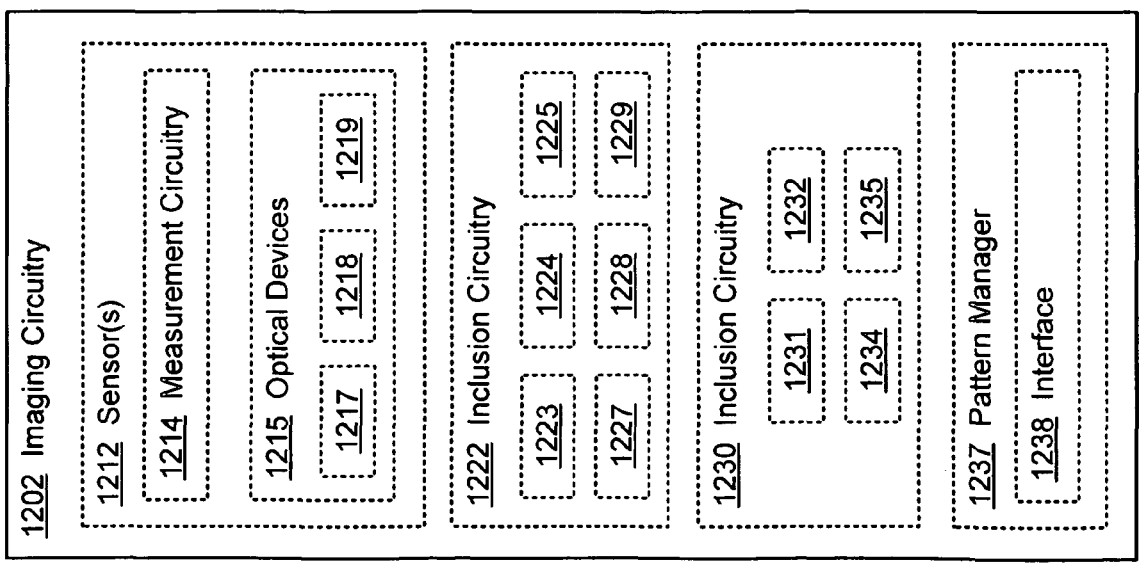
FIG. 12 depicts imaging circuitry in which one or more technologies may be implemented.

Referring now to FIG. 12, there is shown imaging circuitry 1202 such as can be implemented as imaging circuitry 20 of FIG. 1. Imaging circuitry 1202 can include one or more of sensor(s) 1212, inclusion circuitry 1222, inclusion circuitry 1230, or pattern manager 1237. Optical devices 1215 can comprise one or more of fluoroscope 1217, magnetic resonance imaging (MRI) system 1218, or other circuitry 1219. Inclusion circuitry 1222 can comprise one or more of structure indicator 1223, measurement indicator 1224, site indicator 1225, sequencer 1227, material identifier 1228, or other medical information 1229. Inclusion circuitry 1230 can comprise one or more of motion indicator 1231, barcode 1232, photographic record 1234, or other non-medical record 1235. Pattern manager 1237 can include interface 1238.

Figure 13:
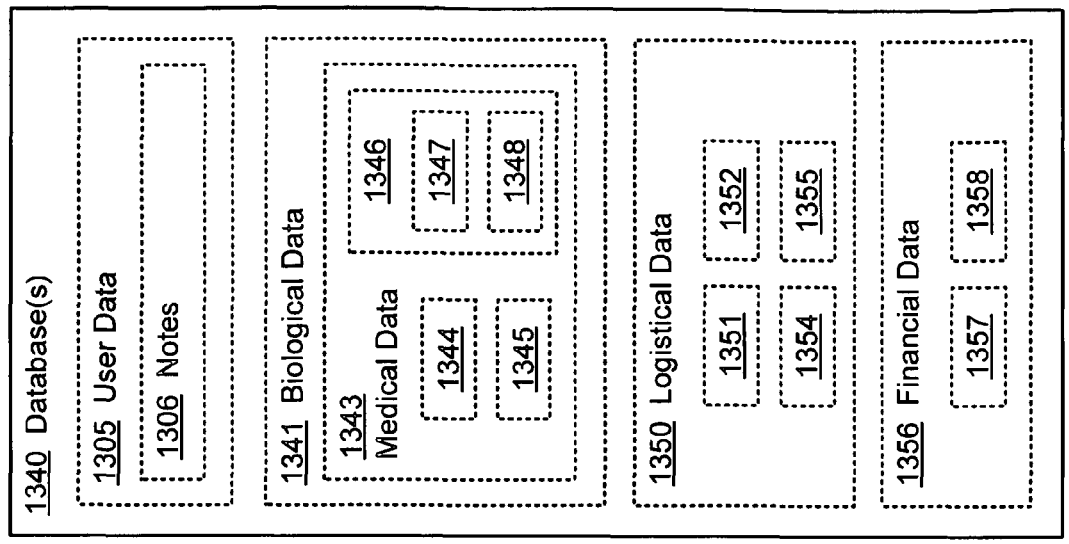
FIG. 13 depicts database(s) in which one or more technologies may be implemented.

Referring now to FIG. 13, there is shown database(s) 1340 that can be used as the one or more databases 140 of FIG. 1. Database(s) 1340 can comprise one or more of user data 1305, biological data 1341, logistical data 1350, or financial data 1356. User data 1305 can include sketches or other notes 1306 which may, of course, include biological or logistical data or the like. Biological data 1341 can, in some embodiments, include medical data 1343. Medical data can comprise one or more of regimen data 1344, pathology data 1345, structural data 1347, position indicator 1348, or other surgical data 1346.

Logistical data 1350 of database(s) 1340 can optionally include one or more of location data 1351, contact data 1352, equipment data 1354, scheduling or other temporal data 1355, or the like. Financial data 1356 can include one or more of insurer data 1357 or other data 1358. In some embodiments, at least medical data 1343 is used in conjunction with inclusion circuitry 1222 or inclusion circuitry 1230.

Figure 14:
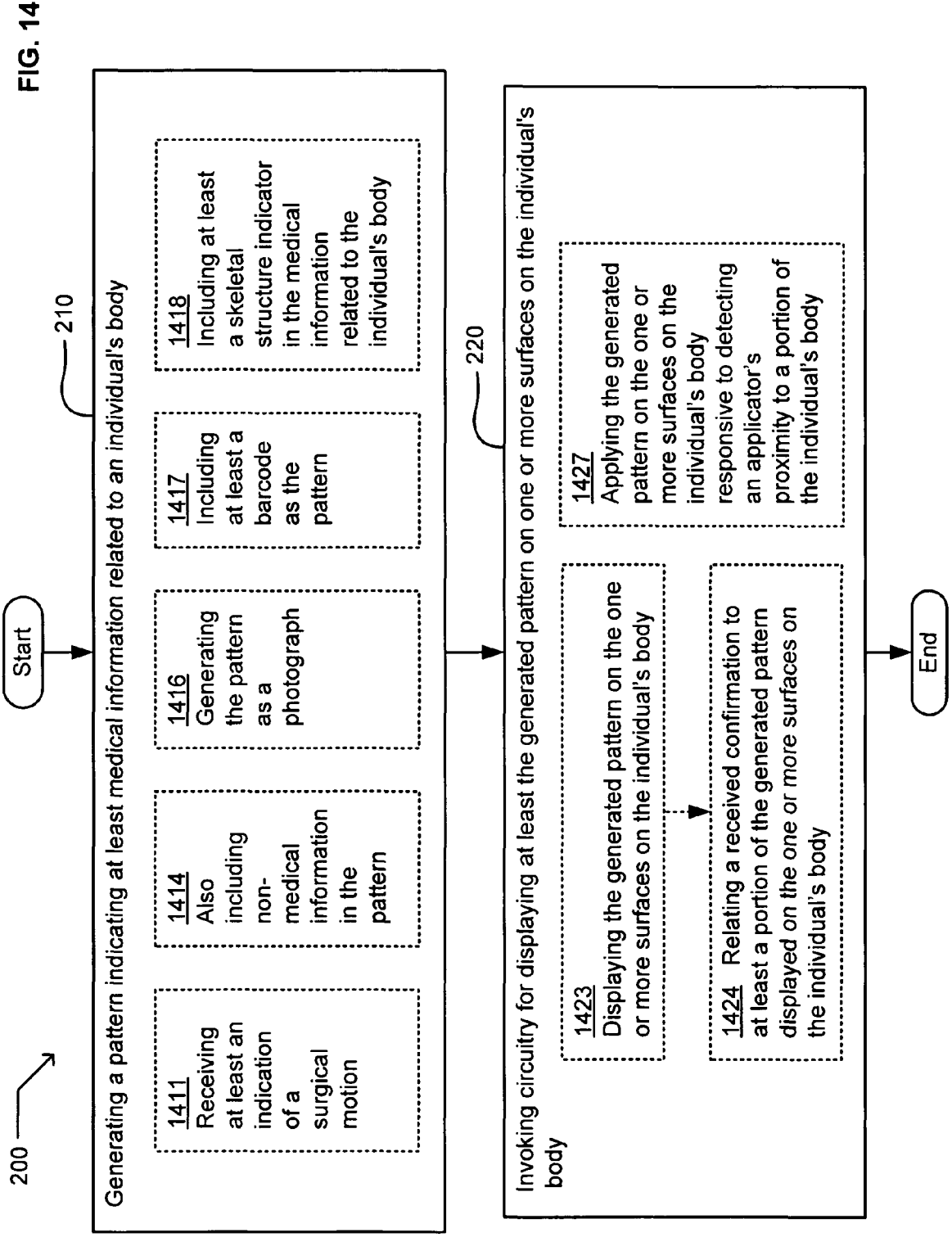

Referring now to FIG. 14, there are shown several variants of the flow 200 of FIG. 2. Operation 210—generating a pattern indicating at least medical information related to an individual's body—may include one or more of the following operations: 1411, 1414, 1416, 1417, or 1418. Operation 220—invoking circuitry for displaying at least the generated pattern on one or more surfaces on the individual's body—may include one or more of the following operations: 1423, 1424, or 1427.

Operation 1411 describes receiving at least an indication of a surgical motion (e.g. pattern manager 1237 receiving "upward" or a depth in motion indicator 1231 from inclusion circuitry 1230). Many such motion indications can be used in describing how a scalpel or laparoscope should move, for example, at a given surgical operation. In another embodiment, sensors 612 detect the motion of stylus 693 directly, for example, as surgeon 620 performs a dry run motion along potential incision site 608. This can occur, for example, in embodiments in which generating circuitry 10 performs flow 200, in which display circuitry 170 is implemented as display circuitry 670, and in which operation 220 is performed by propelling a pigment-containing fluid 731 through stylus 693 or by invoking at least projector 677.

Operation 1414 describes also including non-medical information in the pattern (e.g. inclusion circuitry 1230 including barcode 1232 or other non-medical record 1235 as a pattern in image 111). A pattern including other non-medical record 1235 can, for example, be machine-readable and need not be readable to the naked eye. For example, one or more very small images such as any of those in FIG. 10 can be displayed, in some embodiments, on an eyeball pursuant to many variants of operation 220 described herein. These variants can occur, for example, in embodiments in which generating circuitry 10 of FIG. 1 performs flow 200 and in which imaging circuitry 20 is implemented as imaging circuitry 1202 of FIG. 12.

Operation 1416 describes generating the pattern as a photograph (e.g. inclusion circuitry 1230 including photographic record 1234 within or as image 860). The photograph may be a raw or processed image, and may be obtained as an X-ray, infrared, visible-light or other photographic image from a digital or other capture device. Also the photograph may be all or part of an image, as exemplified in image 111 of FIG. 1.

Operation 1417 describes including at least a barcode as the pattern (e.g. inclusion circuitry 1230 including barcode 1232 within or as image 111). In some embodiments, the barcode can be printed onto skin or another organ surface, or applied to a surface that can then be applied to a body surface as described herein.

Operation 1418 describes including at least a skeletal structure indicator in the medical information related to the individual's body (e.g. inclusion circuitry 1222 adding or otherwise providing structure indicator 1223 or site indicator 1225 as medical information in the pattern). In some embodiments, the medical information in the pattern further includes at least measurement indicator 1224, material identifier 1228, or other medical information 1229. Alternatively or additionally, some or all of these items are excluded from the pattern but are made simultaneously viewable within a common field of view, such as by displaying a subset of them on screen 1195 of hub 1173 to complement the content of image 1180.

Operation 1423 describes displaying the generated pattern on the one or more surfaces on the individual's body (e.g. projection circuitry 374 emitting visible or other energy 575 preferentially through hole 487 of template 460 onto treatment area 587). Substantially a negative of the generated pattern can form template 460, for example, so that the resulting treatment area 587 includes or at least roughly resembles pattern 1062 (a target containing acne or a tumor, e.g.). Those skilled in the art will appreciate that such modes of display are a useful application of a pattern, in some implementations of operation 220.

Operation 1424 describes relating a received confirmation to at least a portion of the generated pattern displayed on the one or more surfaces on the individual's body (e.g. relational circuitry 30 receiving as user input an affirmation of the individual's identity, surgery site, insurer, living will provisions, or the like as presented in a checklist of image 111). In some embodiments, operation 220 can at least begin during a formal procedure and without administering a general anesthetic (e.g. so that a nurse or other user can receive such affirmations orally from the patient). The user can indicate such affirmations using a microphone, a keyboard, a touch screen or the like.

Operation 1427 describes applying the generated pattern on the one or more surfaces on the individual's body responsive to detecting an applicator's proximity to a portion of the individual's body (e.g. an inkjet or other applicator 383 propelling an ink or other colorant toward the one or more surfaces on the individual's body). In some embodiments, the applicator can be a handheld device having a sensor (of sensors 612, e.g.) able to determine whether a printing element is close enough to propel a dot or other marking increment to a printing target. Stylus 693 can optionally be configured to deposit such a marking increment in this manner, for Example, as surgeon 620 repeatedly passes a tip of stylus 693 across the target content (pattern 788, e.g.). In some embodiments, a variant of stylus 693 has a row or grid of orifices like a small inkjet printer. In some embodiments, rather than just forming the pattern by selective material application, a photo-reactive material can be applied to an area surrounding the target and then activated selectively to form the pattern (forming pattern 1162 in a photo-reactive skin covering activated by projection 1175, e.g.).

Referring now to FIG. 15, there are shown several variants of the flow 200 of FIG. 2 or 14. Operation 210—generating a pattern indicating at least medical information related to an individual's body—may include one or more of the following operations: 1513, 1515, 1518, or 1519. Operation 220—invoking circuitry for displaying at least the generated pattern on one or more surfaces on the individual's body—may include one or more of the following operations: 1521, 1523, 1525, 1526, or 1527.

Operation 1513 describes including at least a measurement in the medical information related to the individual's body (e.g. inclusion circuitry 1222 including a blood pressure, a weight history, a heart rate, or the like for use in or with the pattern). The measurement can be measured via measurement circuitry 1214, for example, or downloaded from a network or otherwise retrieved from a medical history associated with the individual.

Operation 1515 describes including at least a site indication in the medical information related to the individual's body (e.g. inclusion circuitry 1222 including "left shoulder," dimensional coordinates, or the like as site indicator 1225). In some embodiments, a hidden portion of the pattern indicates a surgical site, for example, which can be mapped by processing circuitry 390 to apply a visible portion of the pattern to a vicinity of the surgical site.

Operation 1518 describes relating biological information to at least the individual's body (e.g. database 1340 relating "Mr. Thomas Smith" to "sharp pains" as pathology data 1345 and "abdomen" as position indicator 1348). In some embodiments, an individual's location serves as an indication of the individual's body (e.g. "Room C") relating to "critical condition," "next up" for a medical treatment, or some other indicator of a medical triage status. Alternatively or additionally, the biological information can be obtained from one or more other bodies (from other members of a population including the individual, e.g.) and then related to the individual's body.

Operation 1519 describes including, as the medical information related to the individual's body, a portion of the biological information related to at least the individual's body (e.g. pattern 1061, including the above-described triage status or other medical condition, being the generated pattern). In some embodiments, the portion can be selected by the user or automatically in response to an indication of an available resource (a maximum image size, e.g.).

Operation 1521 describes emitting artificial ultraviolet light toward at least an ultraviolet ink portion of the generated pattern (e.g. emitter 377 can include a substantially uniform ultraviolet light beam directed across the entire generated pattern). In some embodiments, operation 1521 can work in conjunction with an image substantially transparent to visible light so as to minimize a social or other non-therapeutic effect of the image upon the individual.

Operation 1523 describes removing at least a portion of the generated pattern from the one or more surfaces on the individual's body (e.g. update circuitry 379 causing an interruption of a projected image). In some embodiments, operation 1523 is performed responsive to a lapse of time and/or a user action. In a transition from a display like that of FIG. 8 to that of FIG. 9, display circuitry 670 removes at least a portion of image 860 roughly contemporaneously with an operation of displaying a successive image 960. These variants can occur, for example, in embodiments in which generating circuitry 10 performs flow 200, in which display circuitry 170 is implemented as display circuitry 670, and in which operation 220 is performed via projector 677 or stylus 693.

Operation 1525 describes projecting the generated pattern (e.g. at least projector 1174 displaying pattern 1162 and image 1180 upon body 1110). These variants can occur, for example, in embodiments in which display circuitry 170 is invoked by operation 220.

Operation 1526 describes changing the projected generated pattern (e.g. update circuitry 1179 configuring projector 1174 to change an orientation, size, or position of pattern 1162 or image 1180 responsive to an indication that user 1120 has moved). In some embodiments, such an indication can be obtained by detecting that one or more reference articles (glasses 1193, e.g.) have moved.

Operation 1527 describes invoking circuitry for reading the generated pattern (e.g. image capture circuitry 397 obtaining a pixel array image of displayed pattern 788 such as by sensors 612). In some embodiments, the circuitry for reading comprises video equipment or other circuitry 1219 of one or more optical devices 1215. Other circuitry 1219 can comprise a Computed Tomography (CT) scanner, for example. Variants of this type can occur, for example, in embodiments in which generating circuitry 10 performs flow 200, in which imaging circuitry 20 is implemented as some or all of the optional (dashed) features of imaging circuitry 1202 as shown, and in which display circuitry 170 is implemented as display circuitry 670.

Referring now to FIG. 16, there are shown several variants of the flow 200 of FIG. 2, 14, or 15. Operation 210—generating a pattern indicating at least medical information related to an individual's body—may include one or more of the following operations: 1611, 1615, 1617, or 1619. Operation 220—invoking circuitry for displaying at least the generated pattern on one or more surfaces on the individual's body—may include one or more of the following operations: 1622, 1623, or 1626.

Operation 1611 describes including an explicit indication of an anomalous material in the medical information related to the individual's body (e.g. inclusion circuitry 1222 indicating via material identifier 1228 a tumor, inflamed tissue, an occlusion, plaque, a foreign object, or the like that can be investigated or acted upon). In some embodiments, inclusion circuitry 1222 further includes one or more of structure indicator 1223, site indicator 1225, or other medical information 1229.

Operation 1615 describes depicting at least a literal anatomical shape in the medical information related to the individual's body (e.g. hub 1173 handling images 1060 comprising photo 1063 or sketch 1064, depicting a blood vessel, muscle, or the like). In some implementations of system 1100, image(s) 1160 are selected and positioned by receiving user inputs (as typed input to hub 1173, e.g.) in lieu of sensor inputs indicating anything about a location of the individual's body 1110.

Operation 1617 describes including at least a user phrase as the medical information related to the individual's body (e.g. relational circuitry 30 relating body 110 to user data 1305 containing notes 1306 including one or more records describing a symptom, question, or situation). This can occur, for example, in embodiments in which imaging circuitry 20 and relational circuitry 30 jointly perform operation 210, in which memory 90 or other relational circuitry 30 contains database(s) 1340, and in which interface 80 performs operation 220 by invoking display circuitry 170.

Operation 1619 describes including at least a portion of one or more anatomical names as the medical information related to the individual's body. (e.g. medical data 1343 naming a blood vessel, a vertebra, a gland, a muscle, an eye or eye part, or the like as pathology data 1345 or structural data 1347).

Operation 1622 describes applying at least an optical masking material as the generated pattern on the one or more surfaces on the individual's body (e.g. printer 386 applying a UV-absorbent paint or the like as masking material 485). In some embodiments, a masking material can be applied to a lamp or other projector rather than in an immediate vicinity of the body; and Operation 1623 describes emitting radiation across a thickness transition of the optical masking material (e.g. lamp 577 displaying a UV image of treatment area 587 on neck skin of individual's body 510 as shown, but not on the nearby skin protected by the material). In some embodiments, the masking material is applied in various effective thicknesses according to an intermediate or other level of masking indicated in the generated pattern.

Operation 1626 describes applying the generated pattern on the one or more surfaces on the individual's body at least partly by propelling a colorant toward the one or more surfaces on the individual's body (e.g. applicator 383 or stylus 693 inkjet-printing or otherwise generating image(s) 1060 as described herein). Alternatively or additionally, one or more other patterns can be applied, before or after, by optical projection or by a transfer template. The transfer template can include an inked raised image, a re-transferable image (like a temporary tattoo, e.g.), an image configured for adhesion to the individual's body, or the like.

Referring now to FIG. 17, there are shown several variants of the flow 200 of FIG. 2, 14, 15, or 16. Operation 210—generating a pattern indicating at least medical information related to an individual's body—may include one or more of the following operations: 1711, 1712, 1714, 1718, or 1719. Operation 220—invoking circuitry for displaying at least the generated pattern on one or more surfaces on the individual's body—may include one or more of the following operations: 1723, 1726, or 1727.

Operation 1711 describes detecting an internal structure of the individual's body (e.g. fluoroscope 1217 or MRI 1218 detecting internal target 1142). In some embodiments, a healthy target 1142 such as a vital organ can be detected in a spatial vicinity of an anomalous internal target. A detected spinal cord and damaged vertebra can be shown in quick alternation or simultaneously in this manner, for example, helping a surgeon or other user better visualize the situation and a course of action.

Operation 1712 describes including, as the medical information related to the individual's body, at least an indication of the detected internal structure of the individual's body (e.g. inclusion circuitry 1222 including as structure indicator 1223 an image of the above-referenced anomalous internal target). Pattern 1162 can include a dually-placed image of target 1142, respectively colored in red and blue for example, functioning in concert with glasses 1193 to give a three dimensional effect for user 1120. In one implementation, emitter 377, mounted on glasses 1193 or otherwise in a vicinity of a viewer, transmits so that both images substantially shine directly toward target 1142. This can greatly diminish a parallax error which might otherwise inhibit effective imaging of target 1142.

Operation 1714 describes including at least an explicit temporal indication in the pattern (e.g. image 111 including a number signifying a date, a weekday, or an estimated time as value 1065). In some embodiments, the temporal indication is an expression of a quantity of time units rather than, for example, a number of cycles per second.

Operation 1718 describes associating a sequential identifier with one or more operational identifiers, in the pattern (e.g. image 111 including "A" & "B" or "1" & "2" as labels of respective operations. In some embodiments, the operational identifier(s) can include a verb form indicating some form of "move," "implanting," "resect," "occlusion," "cleared," "taking" or a similar articulation of a surgical action.

Operation 1719 describes including at least a general indicator of a position of the individual's body as the medical information related to the individual's body (e.g. surgical data 1346 including a sketch of a supine patient, "Operating Room B," or similar location indications as the medical information related to the individual's body). In some embodiments, more than one position is included so that a surgeon or other user can more effectively determine which is most advantageous. This can occur, for example, in embodiments in which imaging circuitry 20 and relational circuitry 30 jointly perform operation 210, in which memory 90 or other relational circuitry 30 contains database(s) 1340, and in which interface 80 performs operation 220 by invoking display circuitry 170.

Operation 1723 describes applying at least the generated pattern as a content portion of a surface-marking template (e.g. printer 386 laser-printing content component 489 of template 460). In some embodiments, such an imaging template can then be used for applying a pattern or allowing a pattern to be applied to the surface of the individual's body (e.g. printer 386 creating a temporary tattoo customized for the individual's body 610). Alternatively or additionally, a lithographic stamp or other raised image can be generated for the individual's body. See, e.g., U.S. patent application Ser. No. 11/086,766 filed Mar. 22, 2005 ("Surgical Site Marking Assembly and Method of Using Same").

Operation 1726 describes applying the generated pattern on the one or more surfaces on the individual's body responsive to detecting another pattern on one or more surfaces on the individual's body (e.g. projector 677 transmitting image 860 responsive to sensors 612 detecting pattern 788 or the pattern of stylus 693 moving along potential incision site 608). These variants can occur, for example, in embodiments in which generating circuitry 10 performs flow 200, and in which display circuitry 170 is implemented as display circuitry 670.

In some embodiments, a template is generated with an alignment component that a person can align with an existing pattern (e.g. applying template 460 to an individual's body 510). Hole 487 can be positioned with accuracy by aligning marks 488 with freckles or similar natural generated markings or the like. These variants can occur, for example, in embodiments in which operation 220 is performed by invoking display circuitry 370, which can implement display circuitry 170 as described above.

Operation 1727 describes systemically inducing an optically detectable epithelial expression (e.g. drip control 385 administering an allergen or other agent effective for modifying an optically detectable attribute of a portion the individual's body's skin). For an allergen having a known association with a recognizable epithelial expression (e.g. hives on the neck, e.g.), the displayed pattern can indicate a measurable response to a regimen for counteracting the allergen. The effectiveness of an antihistamine can be tested, for example, by introducing the drug and the allergen each at various concentrations and by characterizing the response as a concentration of hives per unit of area. In some embodiments, the epithelial expression can similarly be induced artificially by coding a tissue in a target area or otherwise by systemically targeting a protein or other locally concentrated component.

Referring now to FIG. 18, there are shown several variants of the flow 200 of FIG. 2, 14, 15, 16, or 17. Operation 210—generating a pattern indicating at least medical information related to an individual's body—may include one or more of the following operations: 1813, 1815, 1817, or 1819. Operation 220—invoking circuitry for displaying at least the generated pattern on one or more surfaces on the individual's body—may include one or more of the following operations: 1822, 1825, or 1828.

Operation 1813 describes including at least a drug identifier as the medical information related to the individual's body (e.g. medical data 1343 associating a individual's body 1110 with an anesthetic, an opiate, an antihistamine or the like in regimen data 1344). In some embodiments, the identified drug is contraindicated, such as in a phrase like "Allergies: hydrocortisone" as a pattern of image 1180.

Operation 1815 describes including at least an implant identifier as the medical information related to the individual's body (e.g. surgical data 1346 associating a individual's body 610 with an artificial knee, a pacemaker, a conduit or the like in structural data 1347). In some embodiments, more than one eligible implant can be described so that a user can choose which is most advantageous. In some embodiments, the implant identifier refers to an implant already situated inside the individual's body. These variants can occur, for example, in embodiments in which imaging circuitry 20 and relational circuitry 30 jointly perform operation 210, in which memory 90 or other relational circuitry 30 contains database(s) 1340, and in which interface 80 performs operation 220 by invoking display circuitry 170.

Operation 1817 describes including at least an identifier of medical personnel as the medical information related to the individual's body (e.g. logistical data 1350 associating a individual's body 610 with a name of a specific doctor or nurse, an expertise designation like "EEG tech" or "endocrinologist," a list of persons for a surgical operation, or the like). It will be appreciated that such data can constitute important medical information, especially in a case where such personnel or other logistical data 1350 can have an articulable effect on the individual's body. These variants can occur, for example, in embodiments in which generating circuitry 10 performs flow 200, in which display circuitry 170 is implemented as display circuitry 670, and in which operation 220 is performed via projector 677 or stylus 693.

Operation 1819 including an equipment identifier in the pattern (e.g. pattern manager 1237 and database(s) 1340 jointly generating a pattern naming or otherwise depicting a gurney, an ultrasound imaging device, a telephone or other communication device, a cutting instrument, a suture, a pacemaker, a laparoscopic system or the like). In some embodiments, interface 1238 removes one or more of these identifiers from the pattern responsive to user input, such as when a preparatory equipment checklist is complete. These variants can occur, for example, in embodiments in which imaging circuitry 1202 (e.g. as imaging circuitry 20) and database(s) 1340 (of relational circuitry 30) jointly perform operation 210, and in which interface 80 performs operation 220 by invoking display circuitry 170.

Operation 1822 describes displaying the generated pattern on one or more surfaces on the individual's body responsive to a location of a user (e.g. projector 1174 transmitting projection 1175 to a location that depends on whether user 1120 or some other user is a primary user). In some embodiments, a device determines the primary user (e.g. hub 1173 inferring that a wearer of glasses 1193 is the primary user). In some embodiments, hub 1173 or a similar device has input device(s) 1121 comprising a camera and can process an image acquired with it to infer a location or identity of a user. The image can enable an ocular identification, a fingerprint, or some other biometric input, for example.

Operation 1825 describes applying the generated pattern onto skin as the one or more surfaces on the individual's body (e.g. projector 1174 transmitting projection 1175 to skin of the individual's body 1110). Alternatively or additionally, the one or more surfaces can comprise hair, mucous membranes, or the like. These variants can occur, for example, in embodiments in which at least a first process in hub 1173 performs operation 210, in which at least a second process in hub 1173 performs operation 220 so as to invoke at least projector 1174.

Operation 1828 describes projecting the generated pattern (e.g. lamp 577 displaying the generated pattern on an individual's body 510 by projecting a portion of beam 575 constituting the pattern through hole 487). In some embodiments, a translucent or other masking material (material 485, e.g.) forms or modifies the generated pattern by selectively absorbing portion more light on one side of a transition than the other (across perimeter 486, e.g.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Moreover, "can" and "optionally" and other permissive terms are used herein for describing optional features of various embodiments. These terms likewise describe selectable or configurable features generally, unless the context dictates otherwise.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly.

What is claimed is:

1. A treatment system comprising:
   circuitry for generating a pattern indicating at least medical information related to an individual's body;
   an optical masking material configured to be applied as a pattern on one or more surfaces on the individual's body, the optical masking material having one or more holes;
   circuitry for displaying at least the pattern on the one or more surfaces on the individual's body, the circuitry for displaying at least the pattern on the one or more surfaces on the individual's body including:
      circuitry for relating a received confirmation to at least a portion of the pattern displayed on the one or more surfaces on the individual's body; and
      circuitry for emitting artificial ultraviolet light toward at least an ultraviolet ink portion of the pattern, wherein the ultraviolet ink portion of the pattern includes an image transparent to visible light; and
   circuitry for emitting treatment energy through at least one of the one or more holes onto a treatment area, the treatment energy at least partly shielded by the masking material on the one or more surfaces on the individual's body.

2. The treatment system of claim 1 in which the circuitry for displaying at least a pattern on one or more surfaces on the individual's body comprises:
   circuitry for applying the pattern on the one or more surfaces on the individual's body responsive to detecting an applicator's proximity to a portion of the individual's body.

3. The treatment system of claim 1 in which the circuitry for generating a pattern indicating at least medical information related to an individual's body comprises:
   circuitry for including at least a measurement in the medical information related to the individual's body.

4. The treatment system of claim 1 in which the circuitry for generating a pattern indicating at least medical information related to an individual's body comprises:
   circuitry for including an explicit indication of an anomalous material in the medical information related to the individual's body.

5. The system of claim 1 in which the circuitry for relating a received confirmation to at least a portion of the pattern displayed on the one or more surfaces on the individual's body comprises:
   circuitry for presenting an indication of the individual's identity in the pattern displayed on the one or more surfaces on the individual's body; and
   circuitry for receiving an affirmation of the indication of the individual's identity as the confirmation.

6. A treatment system comprising:
   circuitry for generating a pattern indicating at least medical information related to an individual's body;
   an optical masking material configured to be applied as the pattern on the one or more surfaces on the individual's body, the optical masking material having one or more holes;
   circuitry for displaying at least the pattern on the one or more surfaces on the individual's body, the circuitry for displaying at least the pattern on the one or more surfaces on the individual's body including circuitry for emitting ultraviolet light toward at least an ultraviolet ink portion of the pattern, wherein the ultraviolet ink portion of the pattern includes an image transparent to visible light; and
   circuitry for emitting treatment energy through at least one of the one or more holes onto a treatment area, the treatment energy at least partly shielded by the masking material on the one or more surfaces on the individual's body.

7. The treatment system of claim 6 in which the circuitry for generating a pattern indicating at least medical information related to an individual's body comprises:
   circuitry for including at least an explicit temporal indication in the pattern.

8. The treatment system of claim 6 in which the circuitry for generating a pattern indicating at least medical information related to an individual's body comprises:
   circuitry for including at least a user phrase as the medical information realted to the individual's body.

9. The treatment system of claim 1 in which the circuitry for generating a pattern indicating at least medical information related to an individual's body comprises:
   circuitry for including at least a portion of one or more anatomical names as the medical information related to the individual's body.

10. The treatment system of claim 6 in which the circuitry for generating a pattern indicating at least medical information related to an individual's body comprises:
    circuitry for including at least a user phrase as the medical information related to the individual's body.

11. The treatment system of claim 6 in which the circuitry for generating a pattern indicating at least medical information related to an individual's body comprises:
    circuitry for including at least a portion of one or more anatomical names as the medical information related to the individual's body.

12. The treatment system of claim 6 in which the circuitry for generating a pattern indicating at least medical information related to an individual's body comprises:
    circuitry for detecting an internal structure of the individual's body; and
    circuitry for including, as the medical information related to the individual's body, at least an indication of the detected internal structure of the individual's body.

13. The treatment system of claim 6 in which the circuitry for generating a pattern indicating at least medical information related to an individual's body comprises:

circuitry for including at least a barcode as the pattern.

14. The treatment system of claim 6 in which the circuitry for generating a pattern indicating at least medical information related to an individual's body comprises:
   circuitry for including at least a measurement in the medical information related to the individual's body;
   circuitry for including at least a site indication in the medical information related to the individual's body;
   circuitry for including an explicit indication of an anomalous material in the medical information related to the individual's body; and
   circuitry for depicting at least a literal anatomical shape in the medical information related to the individual's body.

15. The treatment system of claim 6 in which the circuitry for displaying at least the pattern on one or more surfaces on the individual's body comprises:
   circuitry for projecting the pattern onto skin as the one or more surfaces on the individual's body responsive to detecting another pattern on the one or more surfaces on the individual's body;
   circuitry for relating a received confirmation to at least a portion of the pattern projected onto the one or more surfaces on the individual's body; and
   circuitry for changing the pattern by removing at least a portion of the pattern from the one or more surfaces on the individual's body.

16. The system of claim 6 in which the circuitry for displaying at least the pattern on one or more surfaces on the individual's body comprises:
   circuitry for applying the pattern on the one or more surfaces on the individual's body at least partly by propelling a colorant toward the one or more surfaces on the individual's body.

17. The treatment system of claim 6 in which the circuitry for generating at least the pattern on one or more surfaces on the individual's body comprises:
   circuitry for including a drug identifier in the medical information related to the individual's body.

18. The treatment system of claim 17 in which the circuitry for generating a pattern indicating at least medical information related to an individual's body comprises:
   circuitry for including, as the medical information related to the individual's body, at least an indication of the detected internal structure of the individual's body;
   circuitry for associating a sequential identifier with one or more operational identifiers, in the pattern; and
   circuitry for including an explicit temporal indication in the pattern.

19. The treatment system of claim 6 in which the circuitry for displaying at least the pattern on one or more surfaces on the individual's body further comprises:
   circuitry for reading an ink drawing of a potential incision site on a patient.

20. The treatment system of claim 6 in which the circuitry for displaying at least the pattern on one or more surfaces on the individual's body further comprises:
   circuitry for determining whether an approval indication of a potential incision site has been received.

21. The treatment system of claim 6 in which the circuitry for displaying at least the pattern on one or more surfaces on the individual's body further comprises:
   circuitry for providing feedback concerning one or more potential incision sites.

22. The treatment system of claim 6 in which the circuitry for displaying at least the pattern on one or more surfaces on the individual's body further comprises:
   display circuitry configured to present feedback concerning one or more potential incision sites proposed by a surgeon.

23. The treatment system of claim 6 in which the circuitry for displaying at least the pattern on one or more surfaces on the individual's body further comprises:
   circuitry for displaying at least a facial image of the individual in the pattern on the one or more surfaces on the individual's body.

24. The treatment system of claim 6 in which the circuitry for displaying at least the pattern on one or more surfaces on the individual's body further comprises:
   an applicator, a handheld device having a sensor configured to determine whether a printing element is close enough to propel a dot or other marking increment to the one or more surfaces on the individual's body.

25. The treatment system of claim 6 in which the circuitry for displaying at least the pattern on one or more surfaces on the individual's body further comprises:
   circuitry for relating a received confirmation to at least a portion of the pattern displayed on the one or more surfaces on the individual's body.

26. The treatment system of claim 25 in which the circuitry for relating a received confirmation to at least a portion on the one or more surfaces on the individual's body comprises:
   a microphone configured to receive verbal input that includes the confirmation.

27. The treatment system of claim 25 in which the circuitry for relating a received confirmation to at least a portion of the pattern displayed on the one or more surfaces on the individual's body comprises:
   one or more media bearing medical data associating the individual's body with an anesthetic.

28. The treatment system of claim 25 in which the circuitry for relating a received confirmation to at least a portion of the pattern displayed on the one or more surfaces on the individual's body comprises:
   one or more media bearing medical data associating the individual's body with an opiate.

29. The treatment system of claim 25 in which the circuitry for relating a received confirmation to at least a portion of the pattern displayed on the one or more surfaces on the individual's body comprises:
   one or more media bearing medical data associating the individual's body with an antihistamine.

30. The treatment system of claim 25 in which the circuitry for relating a received confirmation to at least a portion of the pattern displayed on the one or more surfaces on the individual's body comprises:
   one or more recordable media bearing medical data associating the individual's body with a contraindicated drug.

31. The treatment system of claim 6 in which the circuitry for emitting artificial ultraviolet light toward at least an ultraviolet ink portion of the pattern comprises:
   circuitry for directing an ultraviolet light beam across an entirety of the generated pattern.

* * * * *

UNITED STATES PATENT AND TRADEMARK OFFICE
CERTIFICATE OF CORRECTION

PATENT NO. : 8,442,281 B2  
APPLICATION NO. : 11/414149  
DATED : May 14, 2013  
INVENTOR(S) : Edward K. Y. Jung et al.

Page 1 of 1

It is certified that error appears in the above-identified patent and that said Letters Patent is hereby corrected as shown below:

In the Claims

At Column 16, Line 35, Claim 8, replace "...of claim 6..." with --...of claim 1...--

At Column 16, Line 39, Claim 8, replace "...information realted..." with --...information related...--

At Column 18, Line 62, Claim 31, replace "...of the generated pattern." with --...of the pattern.--

Signed and Sealed this  
Thirteenth Day of August, 2013

Teresa Stanek Rea  
*Acting Director of the United States Patent and Trademark Office*